(12) United States Patent
Alfonso et al.

(10) Patent No.: US 12,156,649 B2
(45) Date of Patent: *Dec. 3, 2024

(54) SUTURE ANCHOR CONSTRUCT AND DEPLOYMENT DEVICE

(71) Applicant: Conmed Corporation, Largo, FL (US)

(72) Inventors: Gregory A. Alfonso, Seffner, FL (US); Matthew C. Summitt, Palm Harbor, FL (US); Robert A. Rofman, St. Petersburg, FL (US)

(73) Assignee: Conmed Corporation, Largo, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/865,723

(22) Filed: Jul. 15, 2022

(65) Prior Publication Data
US 2022/0346769 A1 Nov. 3, 2022

Related U.S. Application Data

(63) Continuation of application No. 15/687,040, filed on Aug. 25, 2017, now Pat. No. 11,395,647.
(Continued)

(51) Int. Cl.
*A61B 17/04* (2006.01)

(52) U.S. Cl.
CPC .. *A61B 17/0401* (2013.01); *A61B 2017/0406* (2013.01); *A61B 2017/0409* (2013.01);
(Continued)

(58) Field of Classification Search
CPC ........ A61B 17/0401; A61B 2017/0406; A61B 2017/0409; A61B 2017/0414; A61B 2017/0417; A61B 2017/0496
See application file for complete search history.

(56) References Cited

U.S. PATENT DOCUMENTS

| | | | |
|---|---|---|---|
| 8,986,327 B2 * | 3/2015 | Karasic | A61B 17/0401 606/144 |
| 2011/0264141 A1 * | 10/2011 | Denham | A61B 17/0401 606/232 |

(Continued)

FOREIGN PATENT DOCUMENTS

| | | |
|---|---|---|
| JP | 2013233435 A | 11/2013 |
| JP | 2014511204 A | 5/2014 |

(Continued)

OTHER PUBLICATIONS

KR Office Action, App. No. 10-2022-7008606, dated Jun. 24, 2022, pp. 3-12.
(Continued)

*Primary Examiner* — Sarah W Aleman
*Assistant Examiner* — Rachel S Highland
(74) *Attorney, Agent, or Firm* — Bond, Schoeneck & King, PLLC; Frederick J. M. Price

(57) ABSTRACT

A soft suture anchor construct is provided for placement in or against tissue or bone. The anchor includes an all-suture anchor having two ends positioned in a first direction in a pre-deployment configuration. In a deployed configuration, the two ends are positioned in a second direction different from the first direction. The suture anchor construct also includes a filament passing through the anchor at a plurality of passing locations, where the filament changes direction at least once along the direction of the longitudinal axis of the anchor and forms at least one slack line. In the pre-deployment configuration, the filament extends a first length between adjacent passing locations, and in the deployed configuration, the filament extends a second length between adjacent passing locations. The second length is shorter than the first length. The suture anchor construct may be (Continued)

deployed in a bone hole with an inserter, anchor driver, or other deployment device.

11 Claims, 15 Drawing Sheets

Related U.S. Application Data

(60) Provisional application No. 62/517,395, filed on Jun. 9, 2017, provisional application No. 62/515,023, filed on Jun. 5, 2017.

(52) U.S. Cl.
CPC .............. *A61B 2017/0414* (2013.01); *A61B 2017/0417* (2013.01); *A61B 2017/0496* (2013.01)

(56) References Cited

U.S. PATENT DOCUMENTS

| | | |
|---|---|---|
| 2012/0290004 A1 | 11/2012 | Lombardo |
| 2013/0110165 A1 | 5/2013 | Burkhart et al. |
| 2013/0190819 A1 | 7/2013 | Norton |

FOREIGN PATENT DOCUMENTS

| | | |
|---|---|---|
| JP | 2015533302 A | 11/2015 |
| KR | 1020130140835 | 12/2013 |

OTHER PUBLICATIONS

AU Examination Report No. 1, App No. 2021254557, dated Oct. 27, 2022, pp. 1-4.

Japanese Office Action, Application No. 2022-077011, dated Apr. 19, 2023, entire document.

* cited by examiner

SUTURE ANCHOR CONSTRUCT AND DEPLOYMENT DEVICE

CROSS-REFERENCE TO RELATED APPLICATIONS

The present application is a continuation of U.S. Non-Provisional Application Ser. No. 15/687,040 filed Aug. 25, 2017 (now U.S. Pat. No. 11,395,647) which claims priority to and the benefit of and U.S. Provisional Patent Application No. 62/515,023 filed on Jun. 5, 2017, and 62/517,395 filed on Jun. 9, 2017.

BACKGROUND OF THE INVENTION

Field of the Invention

The present invention is related to a soft suture anchor construct for fixation in a body including in the extremities and, more particularly, to a soft suture anchor construct with an all-suture anchor securable within a narrow and shallow bone hole.

Description of the Related Art

Anchors are commonly used during surgical procedures to capture and retain objects, such as bony or soft tissue, in a desired attachment location. In particular, conventional all-suture anchors are often utilized to repair soft tissue to bone due to certain benefits of the soft material comprising the all-suture anchor (as should be understood by those of skill in the art). To deploy a conventional all-suture anchor, the anchor is inserted in a pre-formed hole in the bone. Suture or other filament is woven through or secured around the anchor and extends from the anchor and out of the bone hole. The suture or other filament is then used to loop through or otherwise attach to soft tissue (or may already be attached thereto). Therefore, when the suture or other filament is tensioned, the soft tissue and anchor are pulled into a desired position relative to each other.

In many procedures that involve soft tissue fixation in the extremities, for example, it is necessary to have an anchor that can be employed in a shallow hole with a narrow diameter due to the very nature of the location of the procedure. A shallow bone hole requires that the anchor have exceptional retention capacity, because any movement of the anchor away from the shallow bone hole might entirely release the anchor from the bone hole. Numerous factors can influence the retention capacity of a suture anchor. For example, external factors, such as the type of tissue and size of the bone hole, affect the retention capacity of the suture anchor. Other factors related to the anchor's design, such as the size, shape, and material composition, influence the retention capacity as well. Further, the method of deployment of the suture anchor can also influence a suture anchor's retention capacity.

Traditional soft suture anchors for holes in bones are often too large and may extend out of the shallow and narrow bone hole in an extremity. Ill-fitting suture anchors have increased instability and can cause irritation or damage to tissue surrounding the exposed portion of the anchor. Attempts at addressing the problem include scaling down the size of a traditional suture anchor to fit within a shallow and narrow bone hole. However, as the size of the traditional suture anchor decreases, the anchor loses retention capacity and thus is unstable within the bone hole.

In light of the forgoing, the inventors have identified and appreciate a continued need for a suture anchor that provides reliable retention capacity when installed within a shallow and narrow bone hole.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

Embodiments of the present invention recognize that there are potential problems and/or disadvantages with the conventional suture anchors (as discussed herein and above). For example, when conventional suture anchors are scaled down to fit in a narrow bone hole, the scaled down suture anchor loses its retention capacity and is thus more likely to be pulled out of the bone hole. Therefore, a need exists for a simple-to-use soft suture anchor construct having an anchor which is optimally deployed in a shallow and narrow hole in a bone without compromising retention capacity. Various embodiments of the present invention may be advantageous in that they may solve or reduce one or more of the potential problems and/or disadvantages discussed herein.

The present disclosure is directed to an inventive configuration, structure, and resulting function of a soft suture anchor construct. The soft suture anchor construct is provided for placement in, through or against tissue or bone. The anchor can include an all-suture anchor having two ends positioned in/facing a first direction in a pre-deployment configuration. In a deployed configuration, the two ends are positioned in/facing a second direction different from the first direction.

According to another embodiment, a soft suture anchor construct system additionally includes a filament having a first end and a second end. The filament passes through the anchor at passing locations between two ends of the anchor. The filament can preferably pass through the anchor at least at two central passing locations and two longitudinal passing locations. The system may also include an anchor deployment device such as an inserter, anchor driver, or other deployment device having a forked or other similarly shaped tip configured to capture and effectively deploy the anchor (as described further below). The anchor is preferably positioned within the forked tip between two central passing locations for balanced deployment.

According to another aspect, a method is provided for deploying a soft suture anchor construct. The method includes providing a soft suture anchor and a filament having a first end and a second end. The filament passes through the anchor at passing locations between two ends in the anchor. Specifically, the filament can pass through at least two central passing locations and two longitudinal passing locations. After a hole in a bone is prepared, the anchor is passed into the hole by an anchor deployment device. The anchor is in a pre-deployment configuration where the filament extends a first length between adjacent passing locations and the ends of the anchor face a first direction. Thereafter, while still on the tip of an anchor driver in the bone hole, the filament can be tensioned by pulling on at least one end of the filament. As a result of the tensioning, the filament extends a second length between the adjacent passing locations and the ends of the anchor face a second direction different from the first direction. The second length is shorter than the first length such that the anchor is changed to a deployed configuration.

Filament, suture material or sutures, as each term is used and described herein, can include monofilament and braided (i.e., multi-filament) suture as well as any other metallic or non-metallic filamentary or wire-like material suitable for performing the function of a suture. This material can include both bioabsorbable and non-absorbable materials.

Suture anchors, as the term is used herein, can include soft suture anchors formed from filaments of suture material which are retained within pre-formed bone holes by being deformable to increase their diameter to a size greater than that of the bone hole, to thereby reside within the cancellous bone and under the bone cortex. Some embodiments of such a suture anchor and its inherent functionality when deployed in a bone hole is disclosed in U.S. Patent Publication No. 2012/0290004 assigned to the assignee hereof and incorporated by reference herein in its entirety. Since soft anchors are commonly made entirely of suture materials, they are sometimes called "all-suture" anchors, and generally include a fibrous construct anchor body portion (or fibrous, braided or woven fabric-type structure such as a flexible web, as described in U.S. Pat. No. 9,173,652) and a suture or filament portion.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments.

Reference is now made briefly to the accompanying drawings, in which.

DETAILED DESCRIPTION OF THE INVENTION

Figure 1:
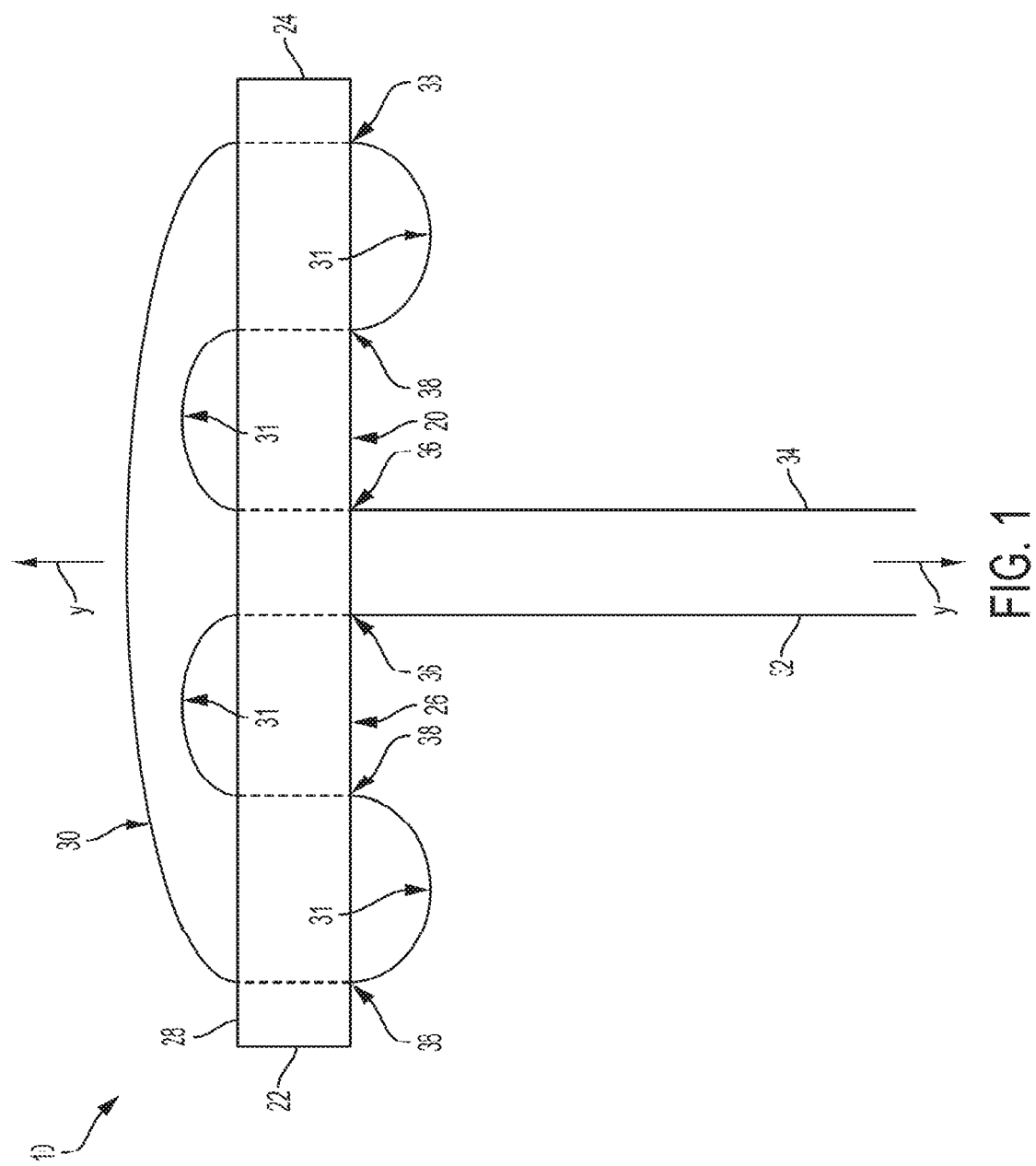
FIG. 1 is a side view schematic representation of a soft suture anchor construct in the pre-deployment configuration according to an embodiment.

Referring now to the drawings, wherein like reference numerals refer to like parts throughout, there is seen in FIG. 1 a side view schematic representation of a soft suture anchor construct 10 according to an embodiment. In the depicted embodiment, the suture anchor construct 10 comprises an anchor 20 having a first end 22 and a second end 24 with a proximal side 26 and a distal side 28 extending therebetween. The anchor 20 depicted in FIG. 1 is an all-suture anchor, which can be composed of either tubular or non-tubular strands of suture. The anchor 20 may also be cylindrical and solid or with a hollow core, and flat or non-flat (as should be understood by those of skill in the art in conjunction with a review of this disclosure). The all-suture anchor 20 is soft for fixation to soft tissue and configured and ultimately positioned to minimize damage to the surrounding tissue and bone (as should be understood by those of skill in the art in conjunction with a review of this disclosure).

The anchor 20 is preferably made out of polyester suture no. 5, because the anchor 20 ideally stays relatively large and rigid in deployment. A polyester suture no. 5 anchor is highly woven and thus denser than a typical Y-Knot® anchor, for example. As an additional advantage, the polyester suture no. 5 anchor 20 is less than 50% the length of a typical Y-Knot® anchor, 18 mm to 40 mm, respectively. As such, the Y-Knot® anchor typically is used in a bone hole that is 20-24 mm, while the anchor 20 depicted in FIG. 1 can preferably be deployed in a narrow bone hole that is approximately 10 mm.

Referring still to FIG. 1, the soft suture anchor construct 10 also comprises a passing filament 30 with a first end 32 and a second end 34 woven through the anchor 20 in a T-shape in the pre-deployment configuration. Different combinations of filament 30 and anchor 20 body sizes are possible as long as the anchor 20 is thicker than the filament 30. In the embodiment shown in FIG. 1, the anchor 20 is a no. 5 suture and the filament 30 is a no. 0 suture. The holding power of the no. 5 suture anchor 20 is greater than the tensile strength of the no. 0 suture filament 30 weaved therethrough. Thus, the no. 0 suture filament 30 will preferably break prior to proximal movement of the no. 5 suture anchor 20, if the no. 5 suture anchor 20 is deployed and fixed in place in a bone hole and the filament 30 is pulled. This property of the deployed anchor 20 minimizes creep toward the top/proximal end of the bone hole. Proximal movement of the deployed anchor 20 in the bone hole is undesirable because the bone hole is relatively small and shallow when formed in the extremities; therefore, slight movement of the anchor 20 might entirely dislodge the anchor 20 from the bone hole. If more tension is placed on the no. 0 suture filament 30, the no. 5 suture anchor 20 is configured to and will widen and wedge into the bottom of the bone hole to lock in place (based on the particular placement of the filament through the anchor, the force and location thereof imparted by the deployment device on the anchor, and the characteristics of the anchor itself. The characteristics of a particular all suture anchor are described, for example, in U.S. 2012/0290004. As described in U.S. 2012/0290004 (e.g., para. [0060] and shown in FIGS. 5 to 6; and also generally shown and described in U.S. Pat. No. 9,173,652), the soft anchor (or "all-suture" anchor) embodiments discussed herein can contain two sections: at least one filament and a fibrous construct (anchor body), which can increase in width, thickness and/or diameter and shrink in length as part of deployment. Even though it is the fibrous construct (anchor) that increases in width, thickness and/or diameter at deployment, it should be understood that the filament also plays a role in the deployment of the anchor. The filament may remain free (in some embodiments) to slide, and non-slidable in others (at least at a particular position or point in use) in relation to the fibrous construct. In brief, the filament helps to position, align and support the fibrous construct (anchor). Examples of other combinations of anchor 20 to filament 30 combinations can include, but are not limited to: a no. 5 anchor with a no. 2 suture, and a no. 2 anchor with a no. 2-0 suture.

In the embodiment shown in FIG. 1a, the passing filament 30 enters and exits the proximal side 26 and distal side 28 of the anchor 20 at a plurality of passing locations 36, 38. In particular, the filament 30 weaves through the anchor 20 at two central passing locations 36 and a plurality of longitudinal passing locations 38 with the first and second ends 32, 34 of the filament 30 extending from the central passing locations 36 on the distal side 26 of the anchor 20. In the embodiment shown in FIG. 1, the filament 30 weaves through the anchor 20 at a total of six passing locations 36, 38 with the longitudinal passing locations 38 between the central passing locations 36 and the first and second ends 22, 24 of the anchor 20. However, in other embodiments, the number of passing locations 36, 38 may vary as long as the first and second ends 32, 34 of the filament 30 both extend from central passing locations 36 and the longitudinal passing locations 38 are between the central passing locations 36 and the first and second ends 22, 24 of the anchor 20.

Figure 2:
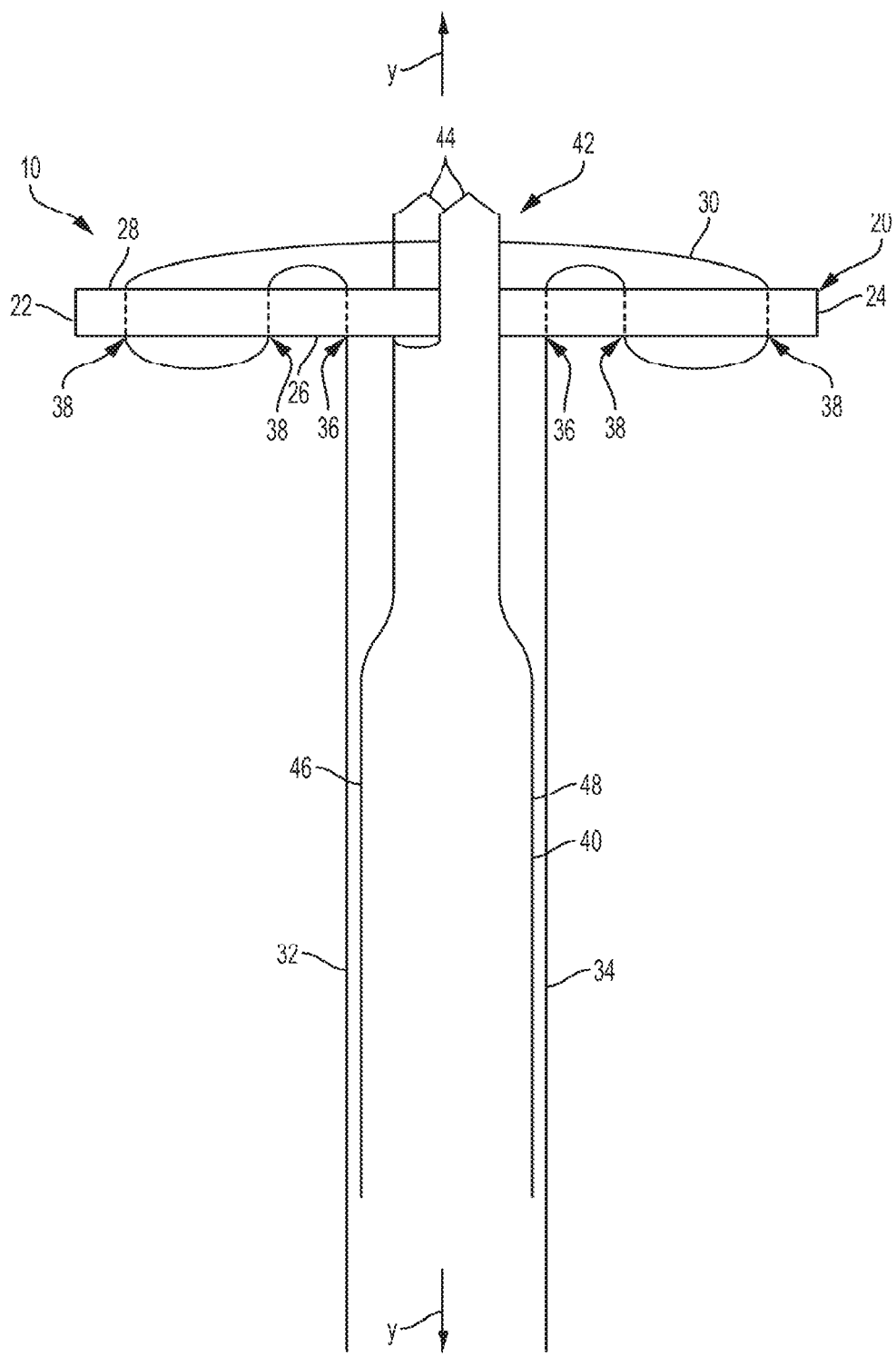
FIG. 2 is a side view schematic representation of the soft suture anchor construct loaded onto an inserter according to an embodiment.

Turning to FIG. 2, there is shown a side view schematic representation of the soft suture anchor construct 10 loaded onto an anchor deployment device/inserter 40 according to an embodiment. As illustrated, the inserter 40 comprises a forked distal tip 42 having a pair of prongs 44. The suture anchor construct 10 is loaded onto the inserter 40 such that the anchor 20 is placed between the pair of prongs 44 on the forked tip 42. In the configuration shown in FIG. 2, the suture anchor construct 10 is loaded on the inserter 40 such that the distal side 28 of the anchor 20 is distally positioned when placed within the forked tip 42. However, in alternative embodiments, the anchor 20 can be loaded between the pair of prongs 44 such that the distal side 28 of the anchor 20 is proximally positioned when placed within the forked tip 42. Importantly, the anchor 20 is positioned within the forked tip 42 such that the first end 32 of the filament 30 extends along a first side 46 of the inserter 40 and second end 34 of the filament extends along a second side 48 of the inserter 40.

Figure 3:
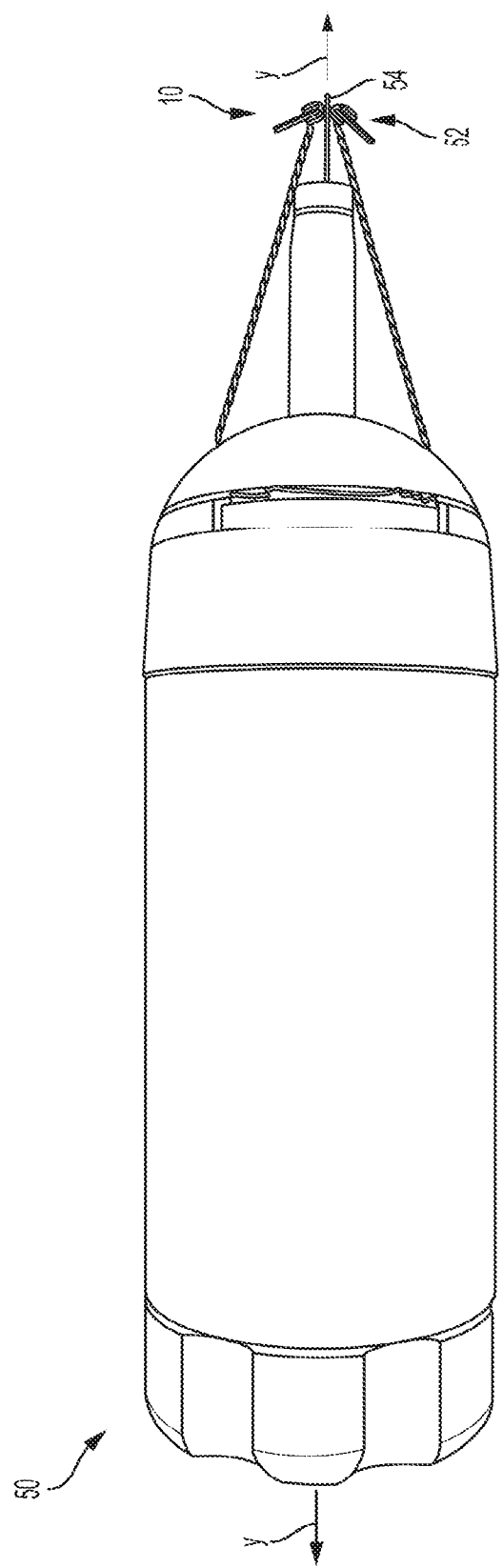
FIG. 3 is a side view schematic representation of the soft suture anchor construct loaded onto a fully assembled deployment device according to an embodiment.
Figure 4:
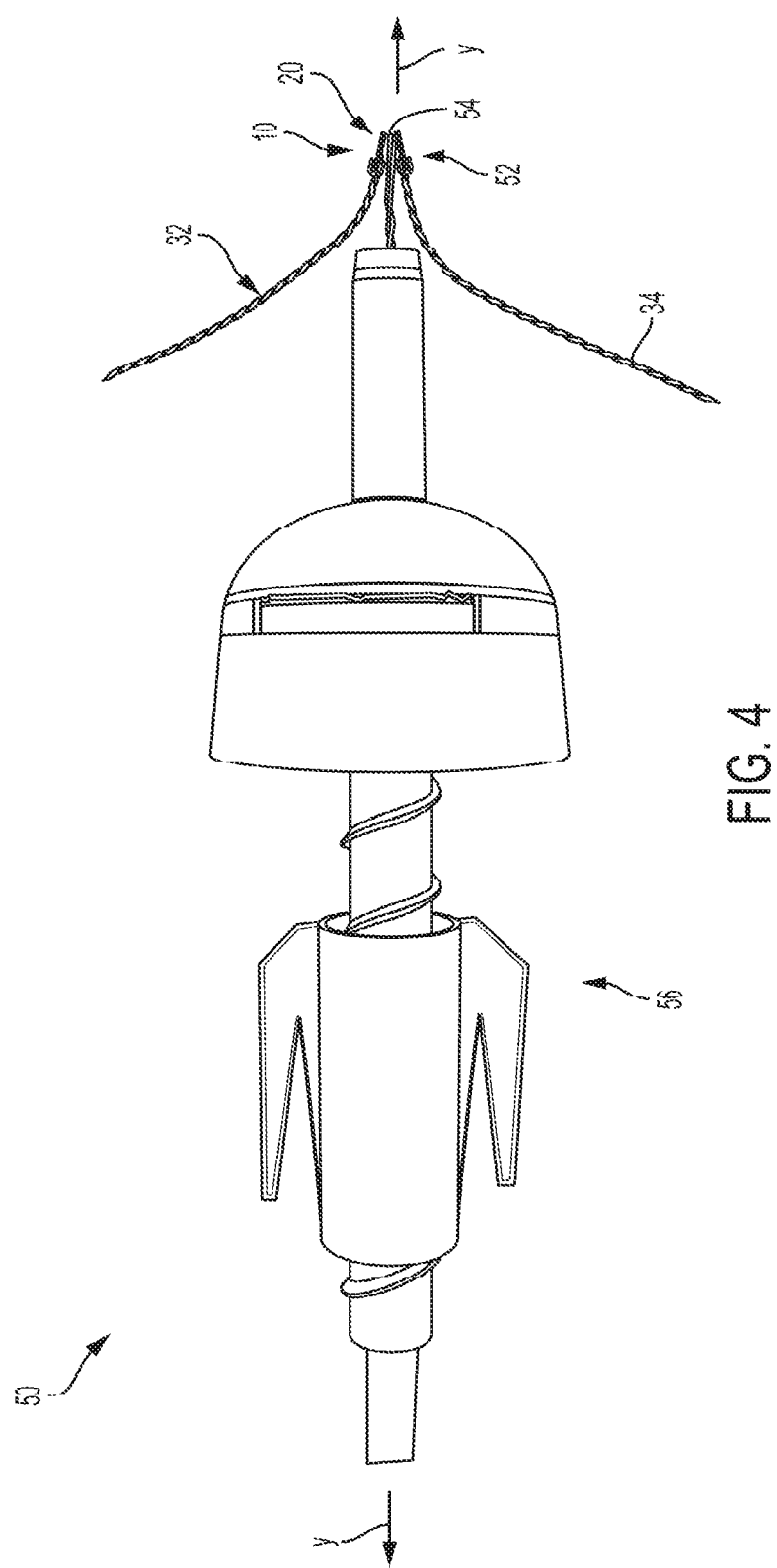
FIG. 4 is a side view schematic representation of a tensioning mechanism of the deployment device, with the outer housing removed, according to an embodiment.
Figure 5:
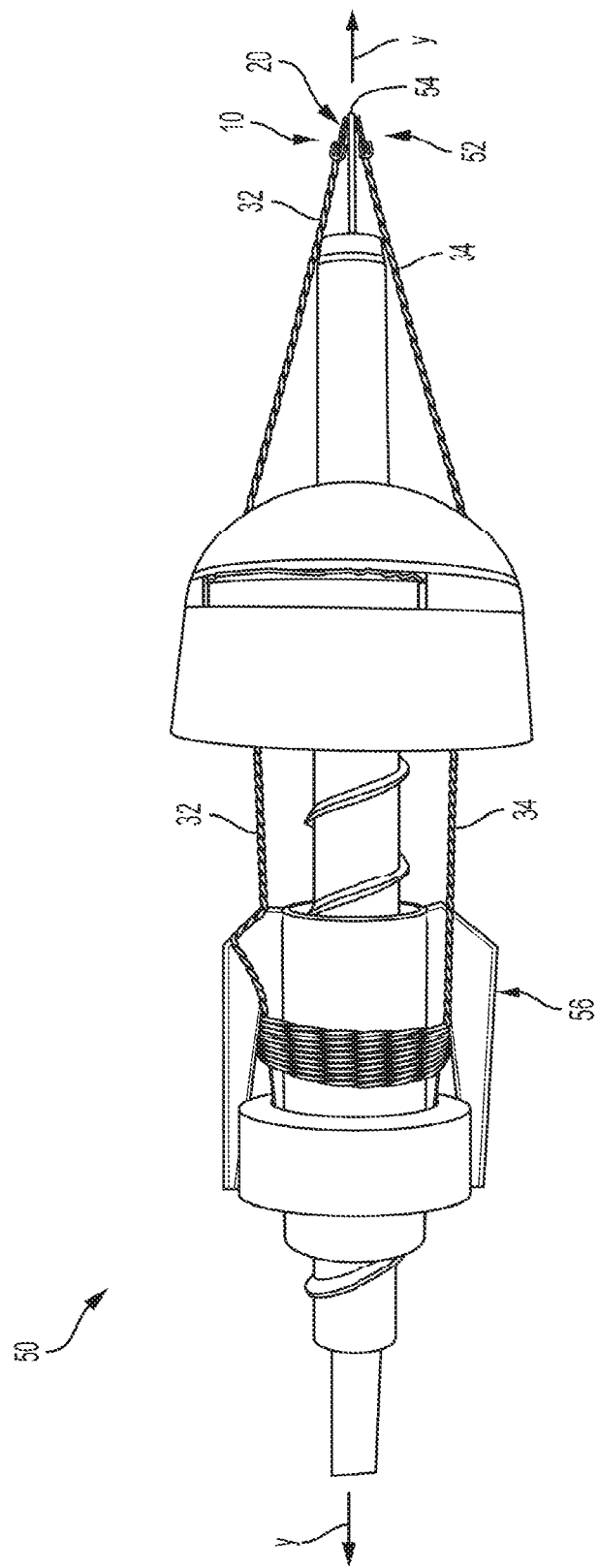
FIG. 5 is a side view schematic representation of the filament of the soft suture anchor construct loaded onto the tensioning mechanism of the deployment device according to an embodiment.
Figure 6:
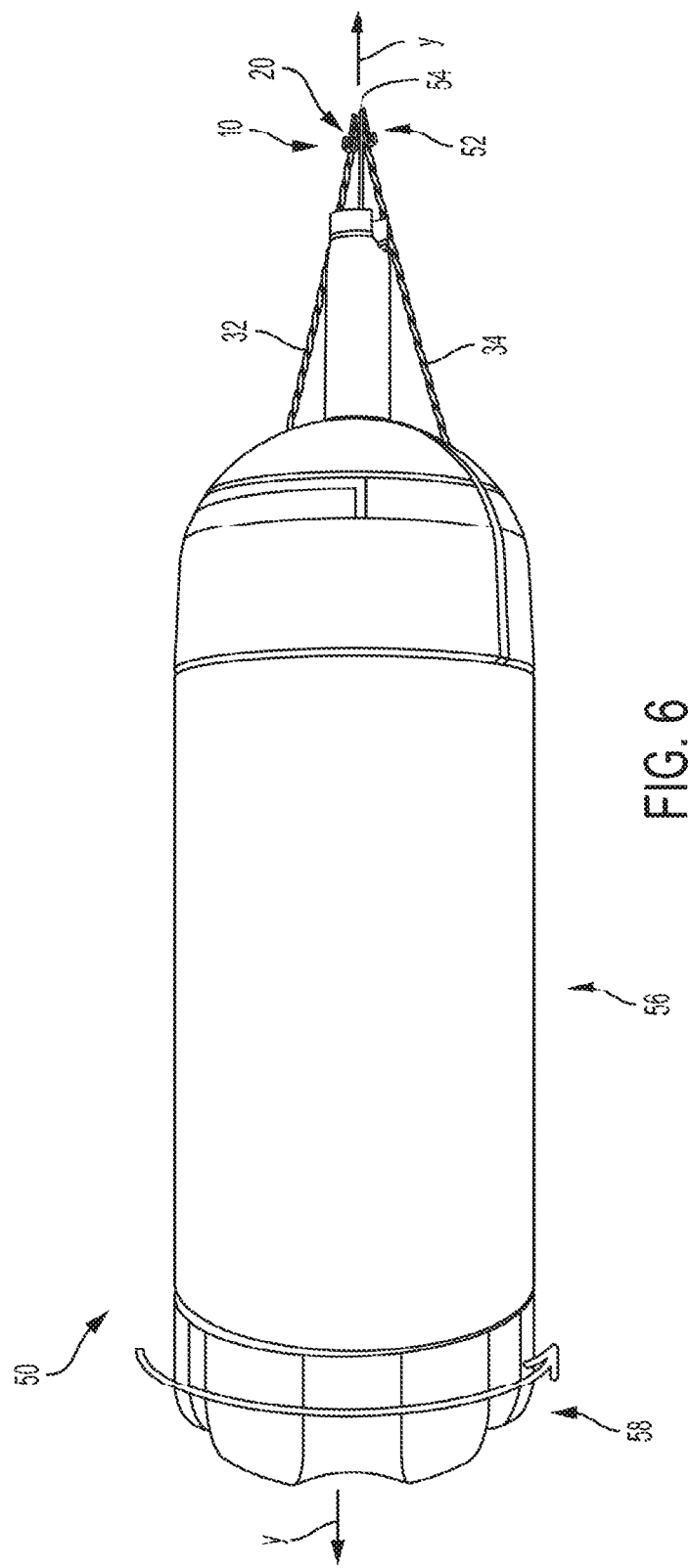
FIG. 6 is a perspective schematic representation of a gear of the tensioning mechanism of the fully assembled deployment device according to an embodiment.

Referring now to FIGS. 3-6, there are shown side view schematic representations of the suture anchor construct 10 loaded on a deployment device 50 according to an embodiment. In brief, FIG. 3 shows a fully assembled deployment device 50 having a body extending along a longitudinal axis y-y, and including a distal tip with the suture anchor construct 10 positioned on the distal end of the distal tip. FIG. 4 shows the deployment device 50 with the outer housing removed, and exposing a tensioning mechanism 56. FIG. 5 shows the deployment device with the outer housing removed, exposing the tensioning mechanism 56, and showing the first and second ends 32, 34 of the filament 30 wrapped around the tensioning mechanism 56. FIG. 6 shows a fully assembled deployment device 50, and axial rotation of gear 58 (shown by the arrow around gear 58), which is configured to move the tensioning mechanism 56 proximally.

In some embodiments, the anchor driver or other deployment device 50 is utilized as an alternative to the inserter 40. Such anchor driver or other deployment device 50 may similarly have a forked tip 52 with a pair of prongs 54 for loading the suture anchor construct 10. The tensioning mechanism 56 holds the first end 32 and second end 34 of the filament 30 in tension and partially at an angle from a longitudinal y-axis (see FIG. 5). The first end 32 and second end 34 of the filament 30 being stably wrapped around the tensioning mechanism 56 maintains the suture anchor construct 10 in the pre-deployment configuration (shown in FIGS. 1-3) so that it can be inserted into a bone hole. After (preferably full) insertion of the distal tip into a bone hole, the suture anchor construct 10 can be deployed by tensioning the first end 32 and second end 34 of the filament 30 (by pulling the first and second ends in the proximal direction away from the distal tip) to fully expand and set/secure the suture anchor construct 10 within the bone hole (preferably at the bottom of the hole). The tensioning mechanism 56, for example, can be used to effectuate this tensioning. In particular, knob, crank, or other gear 58 can be rotated or otherwise actuated (see FIG. 6), to pull the first and second ends 32, 34 of the filament 30 proximally to deploy the suture anchor construct 10 as discussed herein. The first and second ends 32, 34 of the filament 30 can then be released from the deployment device 50, and the deployment device can be removed from the surgical site. The first end 32 and second end 34 of the filament 30 can be further manually pulled distally away from the anchor 20 by a user/medical practitioner, in order to further tension the filament 30 and fully expand and set/deploy anchor 20 within the bone hole, as may be necessary, and finalize the procedure (as should be understood by those of skill in the art in conjunction with a review of this disclosure).

Figure 7:
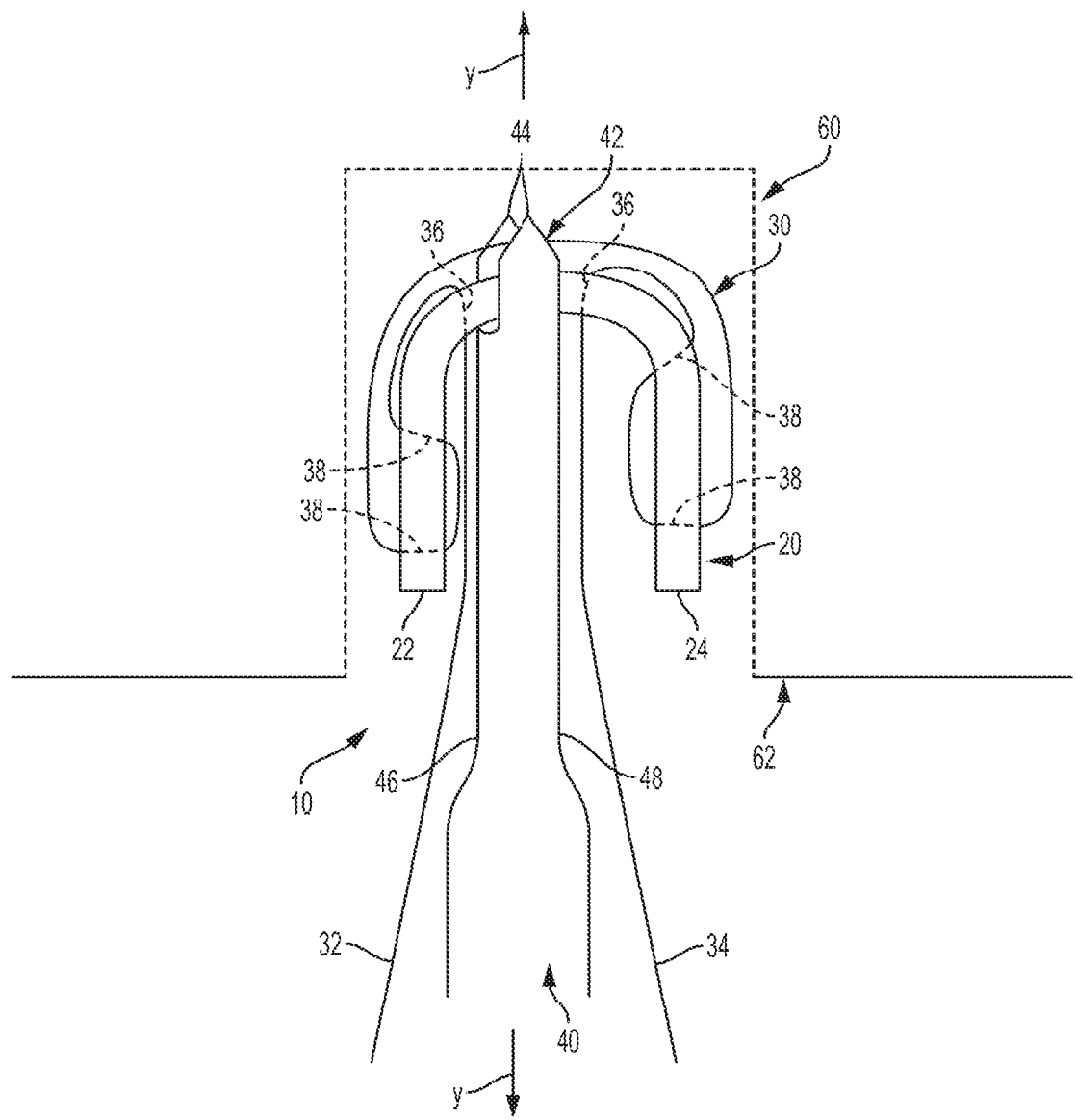
FIG. 7 is a side view schematic representation of the soft suture anchor construct loaded onto an inserter and placed in a bone hole according to an embodiment.

Deployment of the soft suture anchor construct 10 is further described and illustrated with reference to FIGS. 7-13. Referring now to FIG. 7, there is shown a side view schematic representation of the soft suture anchor construct 10 implanted by an inserter 40 into a preformed bone hole 60 according to an embodiment. Once the suture anchor construct 10 is loaded onto the inserter 40 (or other deployment device 50), the inserter 40 is used to push the suture anchor construct 10 into a narrow preformed bone hole 60 (e.g., 10 mm deep). Such a narrow bone hole 60 is often formed in smaller bones by necessity, such as those in extremities. The bone hole 60 can be formed with known methods and instruments, such as through use of a punch or drill.

When the suture anchor construct 10 enters the narrow bone hole 60, the first end 22 and second end 24 of the anchor 20 begin to fold or otherwise bend in the proximal direction toward the surface of the bone 62 due to the narrow width of the bone hole 60. As shown in FIG. 7, the first end 22 of the anchor 20 folds toward the first end 32 of the filament 30 and the first side 46 of the inserter 40, while the second end 24 of the anchor 20 folds toward the second end 34 of the filament 30 and the second side 48 of the inserter 40.

Figure 8:
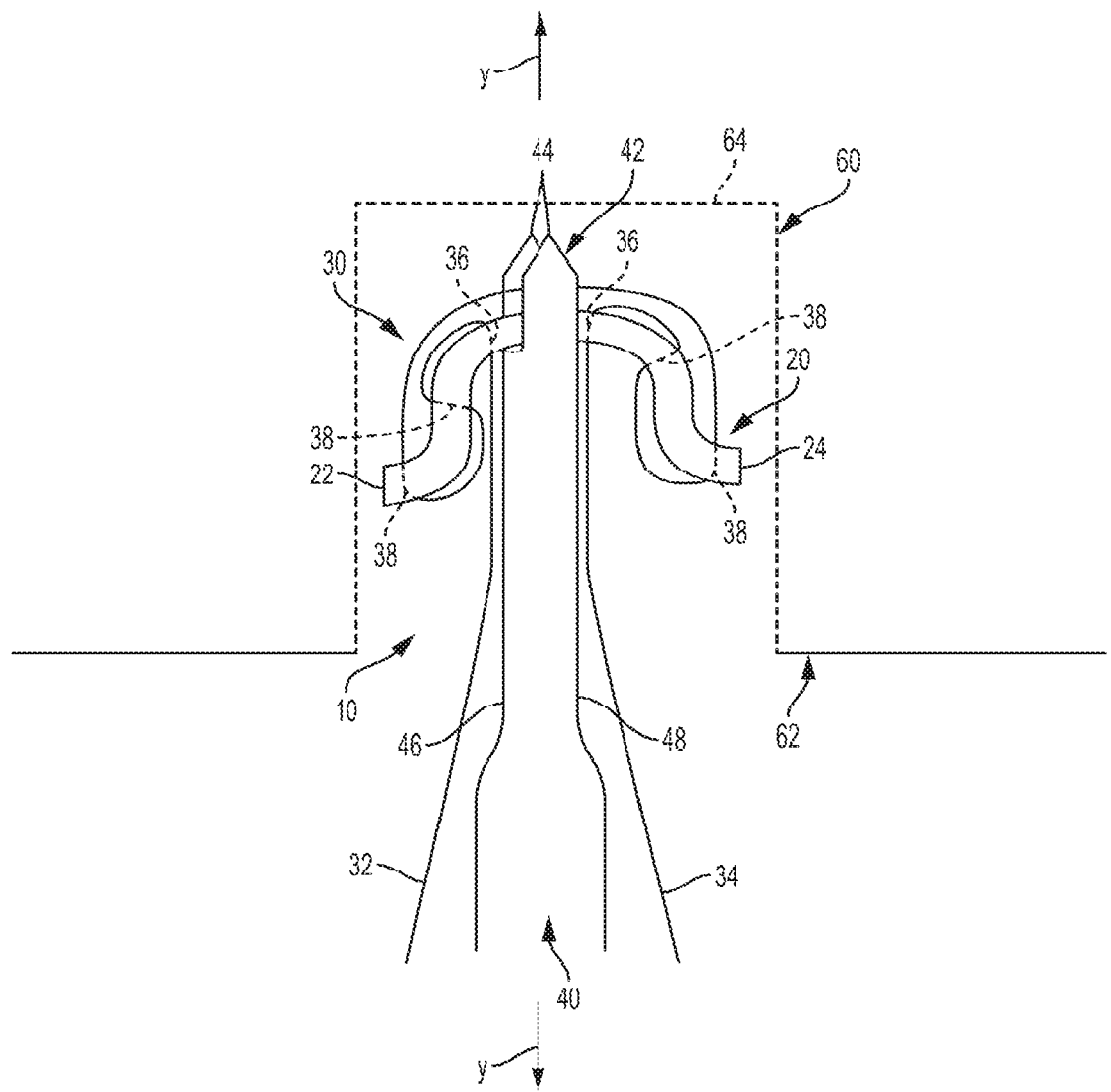
FIG. 8 is a side view schematic representation of the soft suture anchor construct between the pre-deployment and deployed configurations according to an embodiment.

After the suture anchor construct 10 is inserted into the preformed bone hole 60, the suture anchor construct 10 can be deployed. Turning to FIG. 8, there is shown a side view schematic representation of the soft suture anchor construct 10 in the preformed bone hole 60 during deployment. To deploy the suture anchor construct 10, the inserter 40 is held in place, fully inserted in the bone hole 60, while the first and second ends 32, 34 of the filament 30 are tensioned and pulled away from the anchor 20 in the proximal direction. When the first and second ends 32, 34 of the filament 30 are pulled, lengths of anchor 20 between each of the passing locations 36, 38 are pulled closer together as slack in the filament 30 between the passing locations 36, 38 is minimized. Meanwhile, as a result, the first end 22 and the second end 24 of the anchor 20 begin to rotate to face the distal direction toward the bottom 64 of the bone hole 60.

Figure 9:
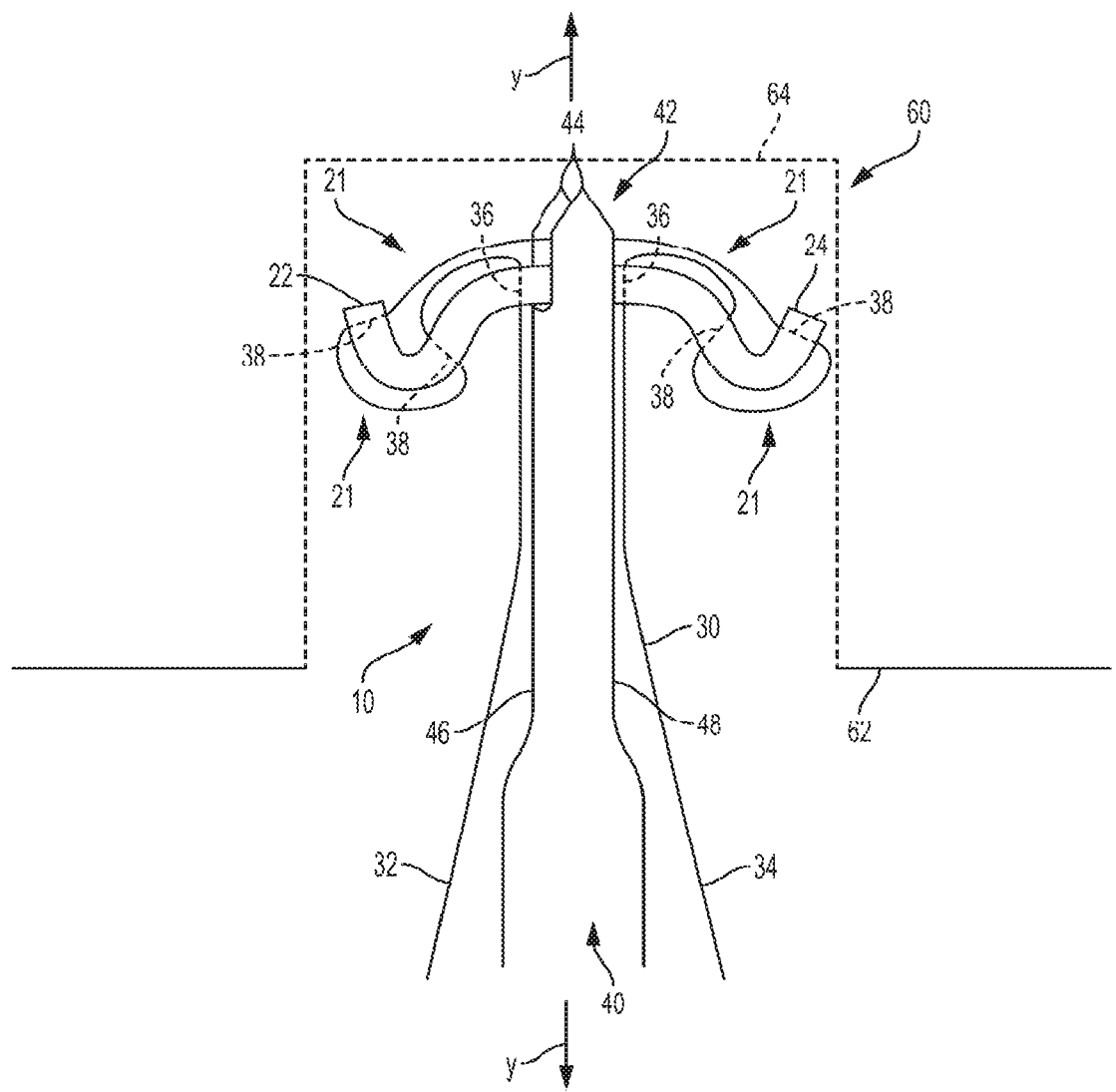
FIG. 9 is another side view schematic representation of the soft suture anchor construct between the pre-deployment and deployed configurations according to an embodiment.

Turning to FIG. 9, there is shown another side view schematic representation of the soft suture anchor construct 10 in the preformed bone hole 60 during deployment. To continue deployment of the suture anchor construct 10, the first and second ends 32, 34 of the filament 30 are pulled farther in the proximal direction away from the anchor 20. Additional slack of the filament 30 between the passing locations 36, 38 in the anchor 20 is reduced when the first and second ends 32, 34 are pulled. As a result, the first and second ends 22, 24 of the anchor 20 continue to fold or otherwise bend tighter until the ends 22, 24 of the anchor 20 face the bottom 64 of the bone hole 60. When the first and second ends 22, 24 of the anchor 20 fold, pleats 21 begin to form between adjacent passing locations 36, 38.

Figure 10:
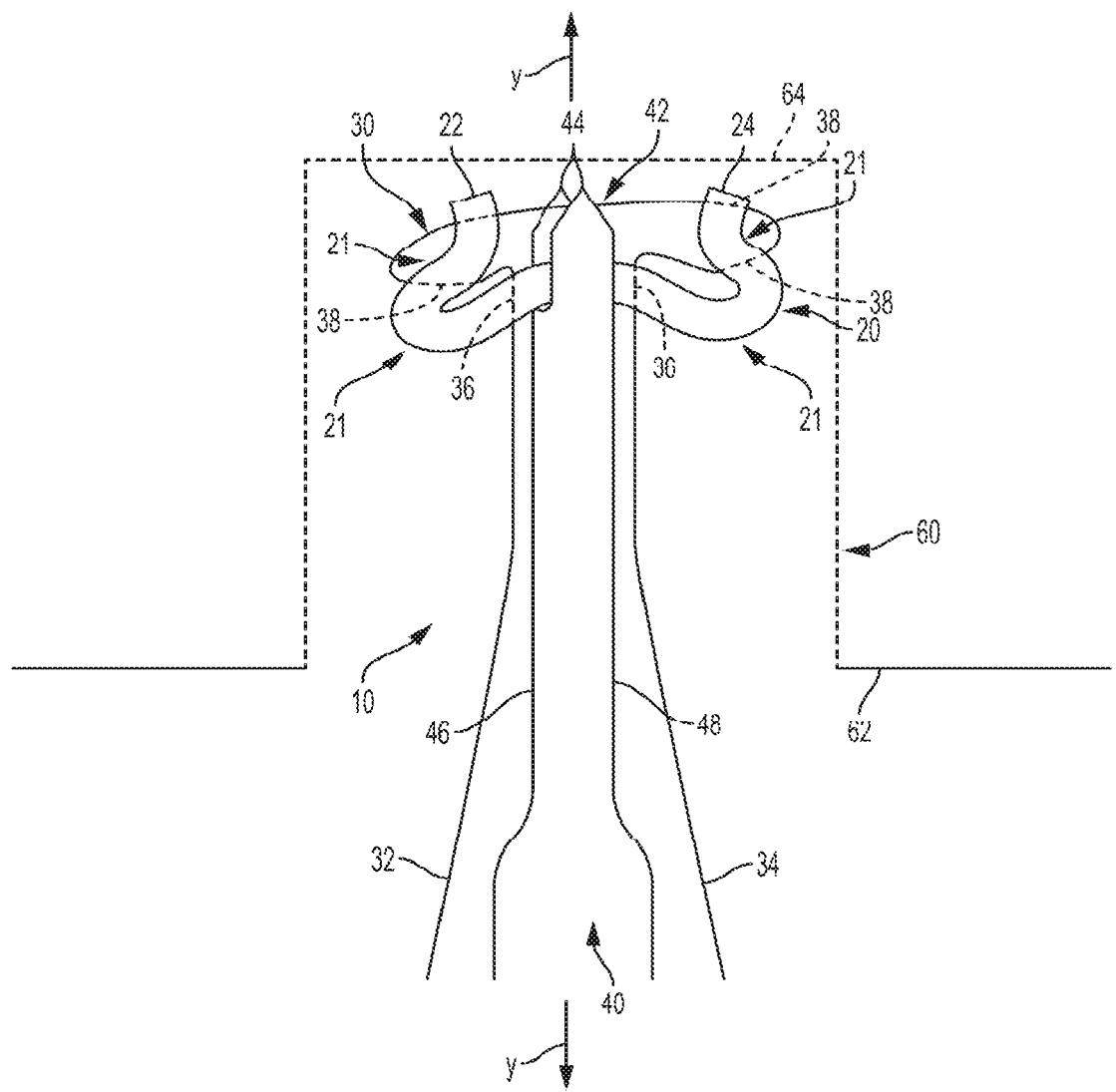
FIG. 10 is a final side view schematic representation of the soft suture anchor construct between the pre-deployment and deployed configurations according to an embodiment.

Referring to FIG. 10, there is shown an additional side view schematic representation of the soft suture anchor construct 10 in the preformed bone hole 60 during deployment. After the first and second ends 22, 24 of the anchor 20 have rotated to face the bottom 64 of the bone hole 60, the first and second ends 32, 34 of the filament 30 are pulled even farther in the proximal direction away from the anchor 20. The added tension again shortens the filament 30 between adjacent passing locations 36, 38 in the anchor 20. Consequently, the first and second ends 22, 24 of the anchor 20 are pulled closer together toward the central longitudinal y-axis through the anchor 20. As an additional result, the pleats 21 between adjacent passing locations 36, 38 become more defined.

Figure 11:
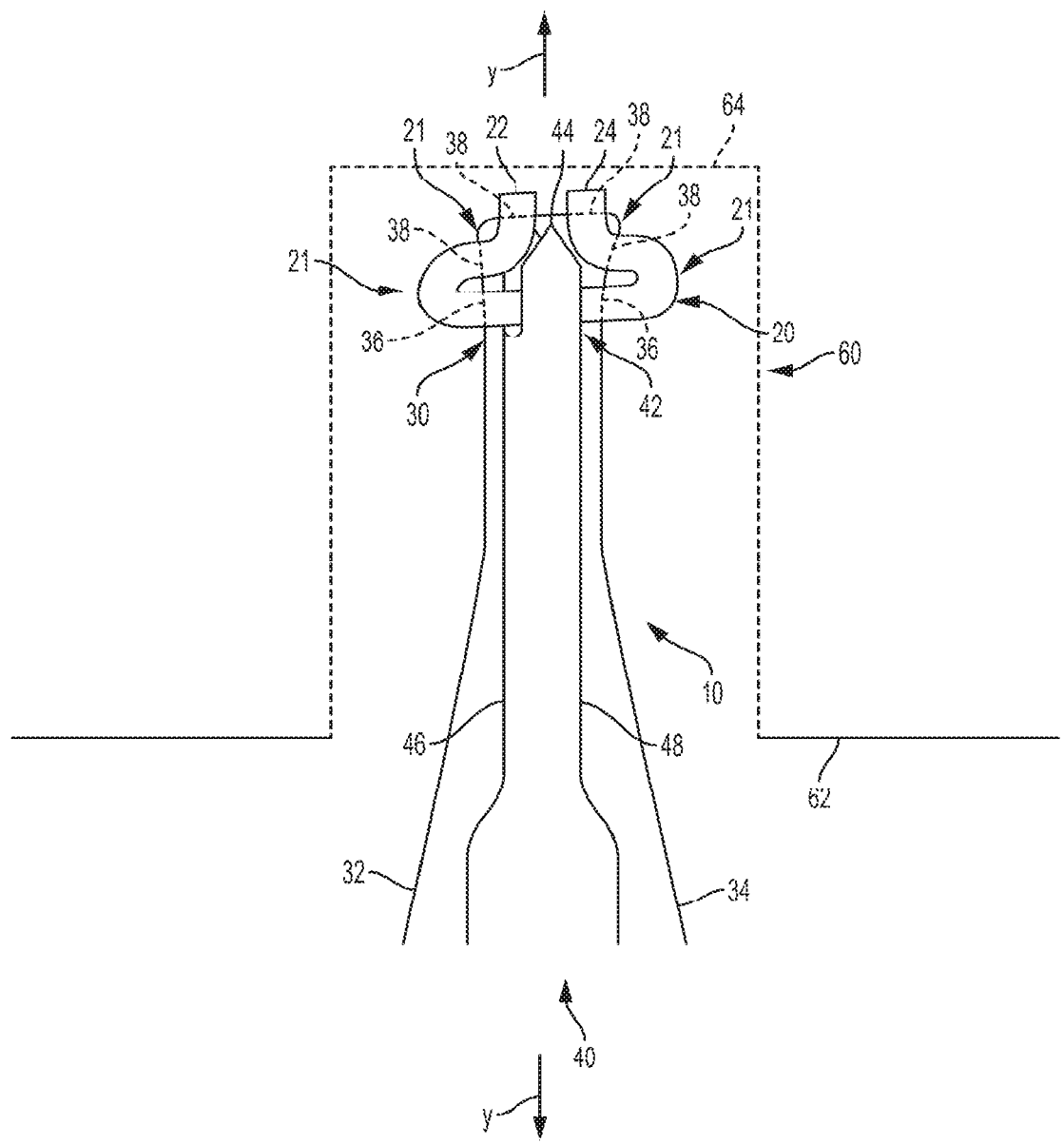
FIG. 11 is a side view schematic representation of the soft suture anchor construct in the deployed configuration according to an embodiment.

Thereafter, the first and second ends 32, 34 of the filament 30 are pulled until there is no remaining slack between adjacent passing locations 36, 38 in the anchor 20, as shown in FIG. 11. In the depicted embodiment, the ends 22, 24 of the anchor 20 face the bottom 64 of the bone hole 60 and are near the central longitudinal y-axis of the anchor 20. As shown, an anchor 20 with six passing locations 36, 38 has four defined pleats 21. Applying additional tension to the ends 32, 34 of the filament 30 strengthens the anchor 20 by forcing the anchor 20 to widen or expand inside the bone hole 60 until it reaches a fully deployed configuration, shown in FIG. 12. In particular, the depicted embodiment shows that as the anchor 20 is compressed or gets shorter, the anchor 20 expands in directions perpendicular to its length (i.e., width or thickness) to set and secure the anchor in place in the bone hole (preferably at or close to the bottom of the bone hole). The pleating reduces the distance between adjacent passing locations 36, 38, as measured along the filament 30, from the first distance 31 (FIG. 1) to the second distance 33, which is relatively shorter than the first distance 31.

The pleats 21 form a stack of the mattress thicknesses effectively increasing a diameter (as measured in relation to the y-axis of the anchor 20 and the bone hole 60). This relative increase in size in distance from the y-axis of the bone hole 60 creates a retention force of the anchor 20, including the expansion in width and/or thickness described above. In other words, Poisson's ratio of width and/or mattress thickness growth during a reduction in length provides for an increase in deployment size that is additive to the increase due to the pleats 21 force of the anchor 20. Poisson's ratio defines a cause and effect relationship where material expands in directions perpendicular to the direction of compression, and conversely, material that is stretched tends to contract in directions transverse the direction of stretching. The ratio defines the proportional decrease in a longitudinal measurement to the proportional increase in length in a sample of material that is elastically stretched. Therefore, if a material is compressed in the x-direction, for example, the material will expand in the y-direction and/or z-direction. An illustration of the utilization of Poisson's ration is shown by a comparison of FIG. 7 (showing the suture anchor construct 10 inserted in the bone hole, but still in a pre-deployment configuration) and FIG. 12 (showing the suture anchor construct 10 in the deployed configuration). Thus, increasing the number of passing locations 36, 38 from the six shown to seven or more is likely to increase the number of pleats 21 and is therefore likely to increase the size of the anchor 20 after deployment. However, a limiting factor is an amount of friction increased by additional passing location 36, 38. Further, the size of the bone hole 60 is an additional limiting factor.

Figure 12:
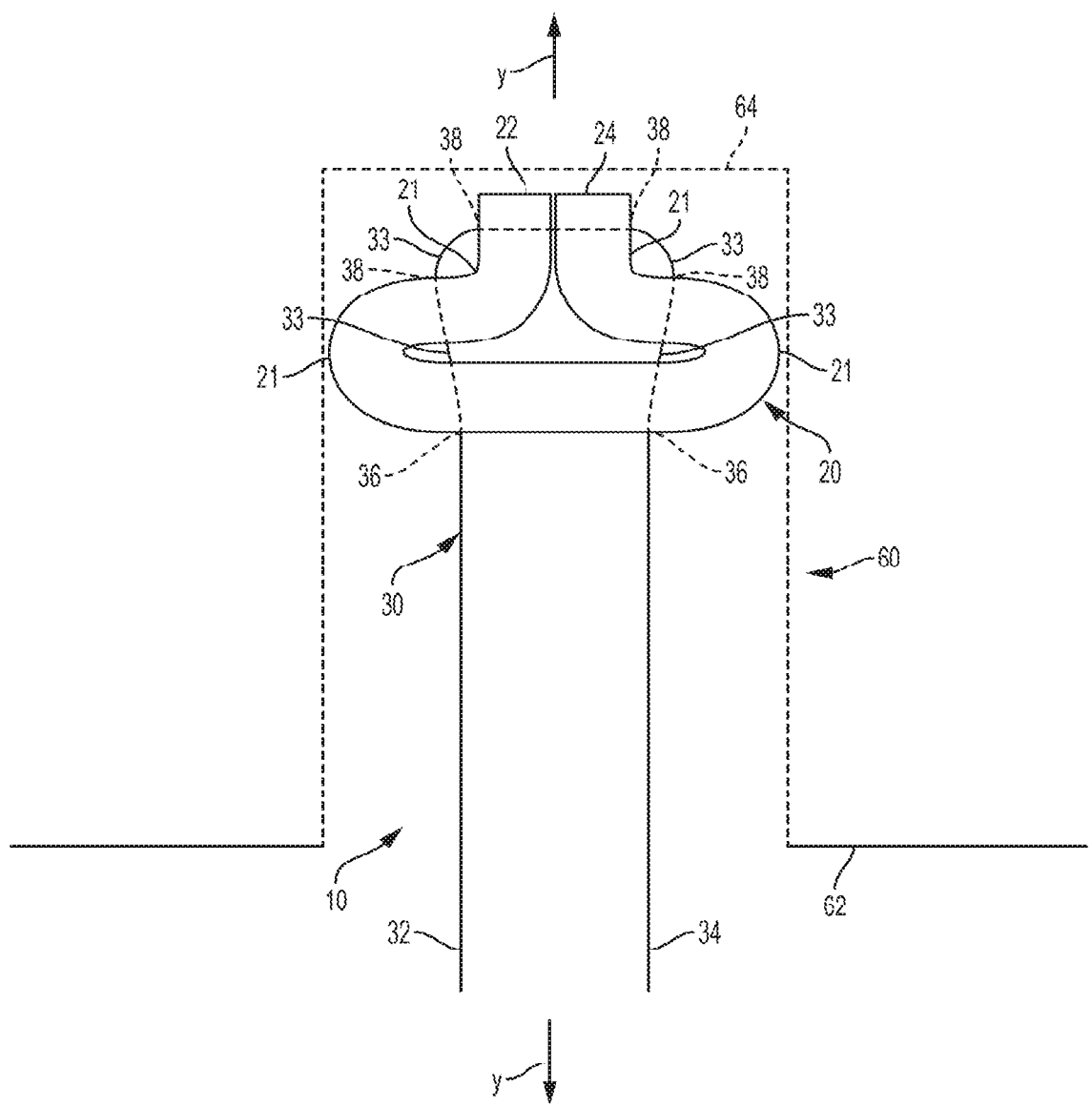
FIG. 12 is a side view schematic representation of the soft suture anchor construct in the fully deployed configuration according to an embodiment.
Figure 13:
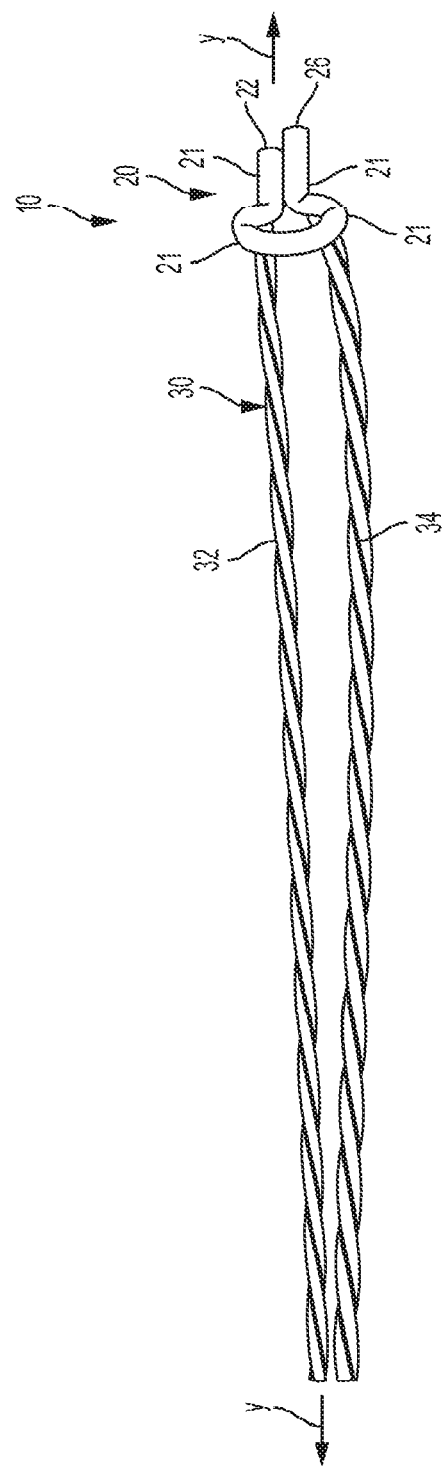
FIG. 13 is a close-up perspective schematic representation of the soft suture anchor construct in the fully deployed configuration according to an embodiment.

Turning to FIG. 12, the suture anchor construct 10 is in the fully deployed configuration with the inserter 40 removed from the suture anchor construct 10 and the bone hole 60. FIG. 13 shows a close-up view of the suture anchor construct 10 outside of the bone hole in the deployed state configuration with the filament 30 extending from the anchor 20. Referring back to FIG. 12, the filament 30 can be removed from the anchor 20 by pulling either the first end 32 or the second end 34 until the entire filament 30 is removed from the bone hole 60. The final form of the anchor 20 in the deployed state allows the filament 30 to easily slide therethrough, as the anchor 20 is set and secured in the bone hole 60. That is, the tensile strength of the anchor 20 in this configuration is sufficient to keep the anchor 20 in place while the filament 30 is easily removed.

Although one particular soft suture anchor construct 10 is shown and further described with respect to FIGS. 1-13, other embodiments of soft suture anchor constructs 10' and 10" are shown and described with respect to FIGS. 14A-D. The ability of the anchor 20 to "ball up" or enter into a deployment configuration when the filament 30 is tensioned is due in part to at least one change/shift in direction of the filament 30 anywhere along a direction of the longitudinal axis x-x of the anchor 20. The ends 32/34 of the filament 30 do not necessarily need to pass through the center and/or near/adjacent the ends 22/24 of the anchor to be configured to form such a deployment configuration construct. In these described embodiments (in addition to the embodiments described above), all that is preferably needed is the at least one change in direction of the filament anywhere along a direction of the longitudinal axis x-x of the anchor 20, in addition to pressure provided between the two filament ends 32/34 (as shown, for example, in a comparison between FIG. 2 and FIG. 11, where an inserter 40 is positioned on the anchor between the filament ends 32/34 capturing portions of the filament and the anchor together, and maintaining a pressure/force in a direction opposite the force of the pulling/tension of the suture ends 32/34 to deploy the anchor).

Figure 14A:
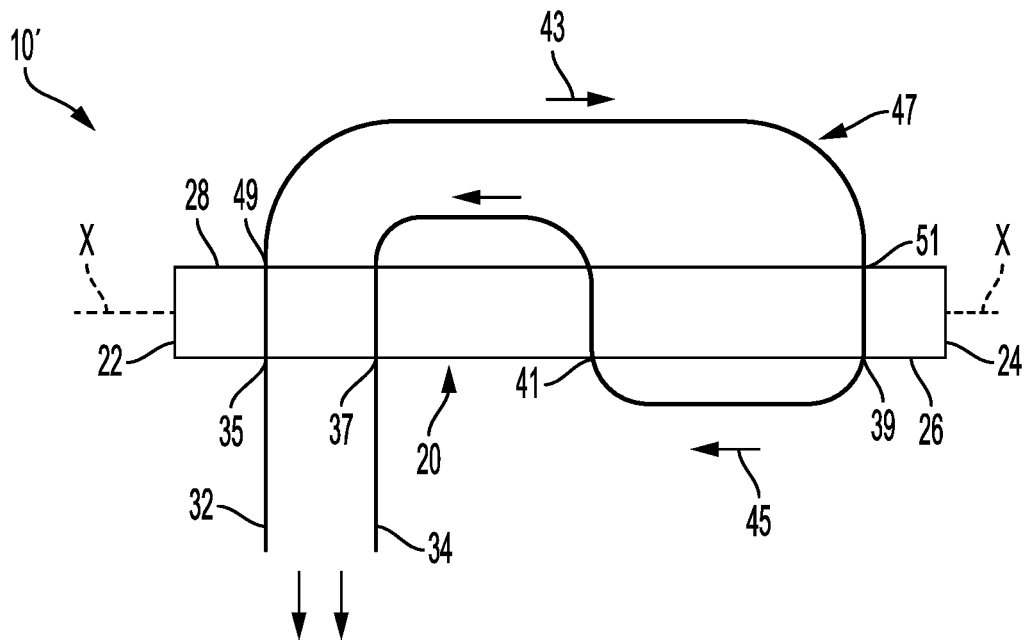
FIG. 14A is a side view schematic representation of a soft suture anchor construct in the pre-deployment configuration according to an embodiment.
Figure 14B:
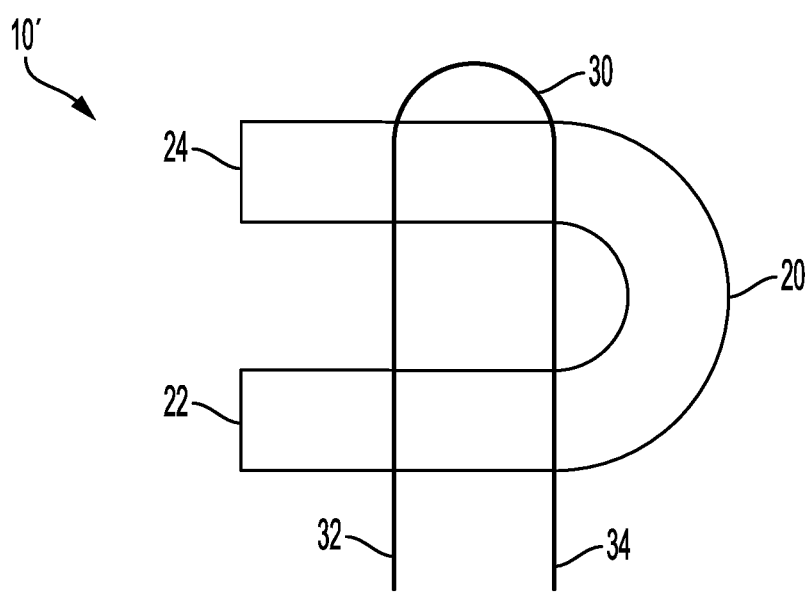
FIG. 14B is a side view schematic representation of the soft suture anchor construct of FIG. 14A in the deployed configuration according to an embodiment.

For example, turning to FIG. 14A, filament 30 is shown starting at first filament end 32 and passing through anchor 20 at passing location 35 near first anchor end 22 from the proximal side 26 to the distal side 28 of the anchor 20. The filament 30 extends in a first direction 43 along an axis parallel to axis x-x towards the second end 24. The filament 30 then passes through the anchor 20 near the second end 24 from the distal side 28 to the proximal side 26 at passing location 39, and continues to extend in a second direction 45 (opposite the first direction). Filament 30 passes through the anchor 20 two more times at passing location 41 (from the proximal side 26 to the distal side 28) and at passing location 37 (from the distal side 28 to the proximal side 26), and ending at second end 34. No matter how many times the filament 30 passes through the anchor 30 (at an angle to the longitudinal axis x-x of the anchor 20), there would still be one change/shift in direction of the filament 30 in FIG. 14A with respect to the longitudinal axis x-x of the anchor 20 as measured from the first end 32 to the second end 34. This change/shift in direction creates at least one slack line 47 (which begins at a point of the beginning of the first direction outside of the anchor at the anchor surface, and ends at the end of the first direction outside of the anchor at the same anchor surface, i.e., at position 49 at the distal side/surface 28 to position 51 at the distal side/surface 28). Due to the opposing forces of the inserter positioned against the anchor 20 between the filament ends 32/34 vs. the pulling of the filament ends 32/34 away from the anchor (as described above), the anchor ends 22 and 24 will bend in the direction toward the largest slack line (here, toward slack line 47) as shown in FIG. 14B. With respect to any embodiment, the "largest slack line" is the slack line that is longest in length (singular—see FIG. 14A, or additive/combination—see FIG. 14C) on one side 26/28 of the anchor 20. For example, the largest and only pertinent slack line in FIG. 14A is slack line 47, which is created by filament end 32 extending through passing location 35, exiting distal end 28 at point 49, extending away from the anchor end 22 to which it is closest, and ending at point 51 at the beginning of passing location 39.

Figure 14C:
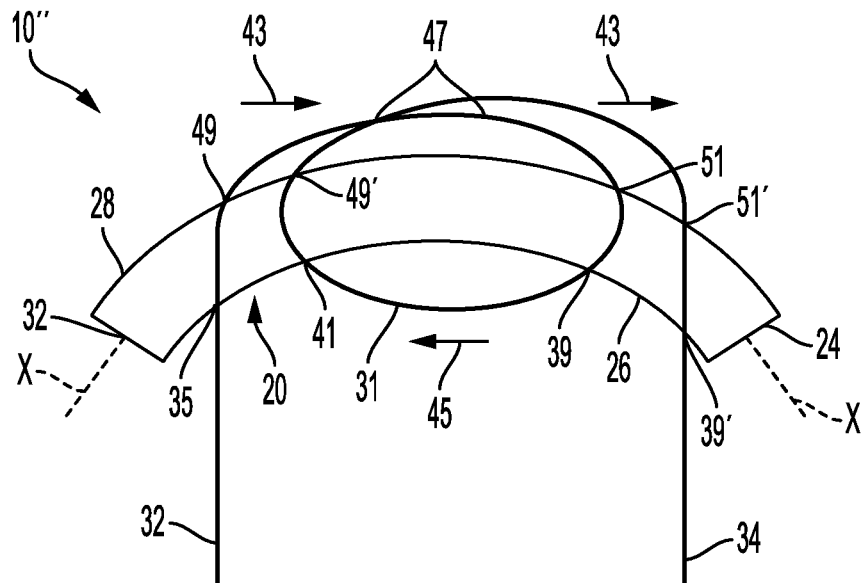
FIG. 14C is a side view schematic representation of a soft suture anchor construct in the pre-deployment configuration according to an embodiment.
Figure 14D:
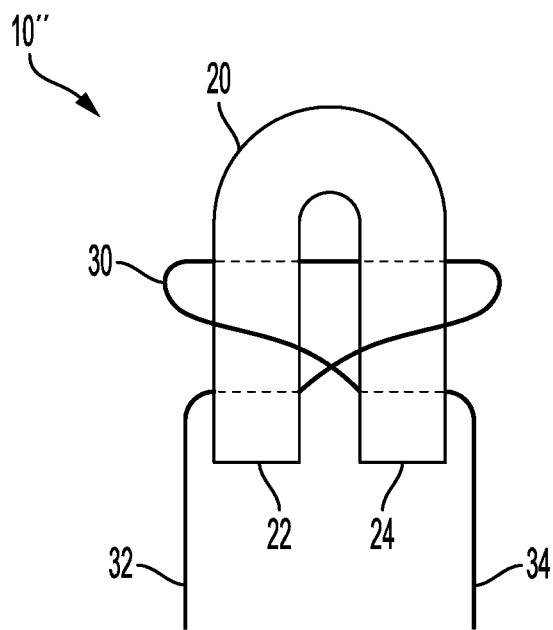
FIG. 14D is a side view schematic representation of a soft suture anchor construct of FIG. 14C in the deployed configuration according to an embodiment.

Turning to FIG. 14C, a two changes in direction embodiment is shown (a two changes in direction embodiment is also shown with respect to FIGS. 1-13). In brief, filament 30 is shown starting at first filament end 32 and passing through anchor 20 at passing location 35 near first anchor end 22 from the proximal side 26 to the distal side 28 of the anchor 20. The filament 30 extends in a first direction 43 along an axis parallel to axis x-x towards the second end 24. The filament 30 then passes through the anchor 20 from the distal side 28 to the proximal side 26 at passing location 39, and continues to extend in a second direction 45 (opposite the first direction). Filament 30 then passes through the anchor 20 at passing location 41 (from the proximal side 26 to the distal side 28) and extends back toward second anchor end 24. The filament 30 continues to extend in a first direction 43 along an axis parallel to axis x-x towards the second end 24. The filament 30 then passes through the anchor 20 from the distal side 28 to the proximal side 26 at passing location 39', and continues to extend in the proximal direction forming second filament end 34. No matter how many times the filament 30 passes through the anchor 30 (at an angle to the longitudinal axis x-x of the anchor 20), there would still be two changes/shifts in direction of the filament 30 in FIG. 14C with respect to the longitudinal axis x-x of the anchor 20 as measured from the first end 32 to the second end 34. These changes/shifts in direction create at two slack lines 47 and 51 (slack line 47 being the largest, as it includes the combination of two loops). Due to the opposing forces of the inserter positioned against the anchor 20 between the filament ends 32/34 vs. the pulling of the filament ends 32/34 away from the anchor (as described above), the anchor ends 22 and 24 will bend in the direction toward the largest slack line (here, toward combined slack line 47) as shown in FIG. 14D.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements. 13

What is claimed is:

1. A soft suture anchor construct, comprising:
an all-suture anchor extending along a longitudinal axis and having a top surface, a bottom surface, a first anchor end and a second anchor end positioned in a first direction in a pre-deployment configuration; and
wherein the first anchor end and the second anchor end are positioned in a second direction different from the first direction in a deployed configuration,
further comprising a filament woven through the all-suture anchor at a plurality of passing locations,
wherein the filament has a first filament end and a second filament end, at least one of which extends from a first passing location proximate to either the first anchor end or the second anchor end, and
wherein the filament partially extends in a first direction substantially along the longitudinal axis, followed by a change in direction, extension through the top surface and the bottom surface of the anchor, and partial extension in a second direction opposite to the first direction and substantially along the longitudinal axis, and followed by a change in direction, extension through the bottom surface and the top surface of the anchor, and partial extension in a third direction opposite to the second direction and substantially along the longitudinal axis in the pre-deployed configuration.

2. The suture anchor construct of claim 1, wherein the second end of the filament extends from a second passing location adjacent to the first passing location.

3. The suture anchor construct of claim 2, wherein the filament passes through a third passing location proximate to the center of the all-suture anchor and a fourth passing location at the second anchor end from the first anchor end proximate to the first passing location.

4. The suture anchor construct of claim 3, wherein the filament extends from the first filament end passing through the first passing location through the fourth passing location to define a slack line therebetween having a first length.

5. The suture anchor construct of claim 4, wherein the filament extends from the fourth passing location to the third passing location to define a second slack line having a second length that is less than the first length.

6. The suture anchor construct of claim 5, wherein the filament extends from the third passing location to the second passing location.

7. The suture anchor construct of claim 1, wherein the second filament end extends from a second passing location adjacent to the second anchor end.

8. The suture anchor construct of claim 7, wherein the filament passes through a third passing location on a first side of the all-suture anchor proximate to the first passing location and though a fourth passing location on an opposing side of the all-suture anchor proximate to the second passing location.

9. The suture anchor construct of claim 8, wherein the filament extends from the first filament end passing through the first passing location through the fourth passing location to define a slack line therebetween having a first length.

10. The suture anchor construct of claim 9, wherein the filament extends from the fourth passing location to the third passing location to define a second slack line having a second length that is less than the first length.

11. The suture anchor construct of claim 10, wherein the filament extends from the third passing location to the second passing location to define a third slack line.

\* \* \* \* \*